(12) United States Patent
Greer

(10) Patent No.: US 6,700,394 B2
(45) Date of Patent: Mar. 2, 2004

(54) DEVICE FOR USE IN MONITORING PARTICULATE FLOW

(75) Inventor: David G. Greer, Cambridge, MN (US)

(73) Assignee: AgriChem, Inc., Ham Lake, MN (US)

( * ) Notice: Subject to any disclaimer, the term of this patent is extended or adjusted under 35 U.S.C. 154(b) by 0 days.

(21) Appl. No.: 10/149,345
(22) PCT Filed: Jan. 25, 2001
(86) PCT No.: PCT/US01/02512
  § 371 (c)(1), (2), (4) Date: Jun. 7, 2002
(87) PCT Pub. No.: WO01/55736
  PCT Pub. Date: Aug. 2, 2001

(65) Prior Publication Data
US 2002/0190731 A1 Dec. 19, 2002

Related U.S. Application Data
(60) Provisional application No. 60/178,268, filed on Jan. 27, 2000.

(51) Int. Cl.[7] ............................................. G01R 27/26
(52) U.S. Cl. .................. 324/686; 324/664; 324/689; 73/861.73; 56/10.2 B
(58) Field of Search .................. 324/634, 640, 324/663, 664, 686, 689, 694; 56/10.2 B, 10.2 R; 73/861, 861.73, 861.71

(56) References Cited

U.S. PATENT DOCUMENTS

| | | | |
|---|---|---|---|
| 2,611,974 A | 9/1952 | Stratveit et al. | 34/454 |
| 3,593,128 A | 7/1971 | Perry | 324/666 |
| 3,784,905 A * | 1/1974 | Blackwell | 324/663 |
| 3,792,457 A | 2/1974 | Templeton et al. | 324/252 |
| 4,748,400 A | 5/1988 | Typpo | 324/670 |
| 4,791,353 A | 12/1988 | Typpo | 324/667 |
| 4,955,270 A | 9/1990 | Volk, Jr. | 73/861.73 |
| 5,959,218 A | 9/1999 | Strubbe | 73/861.71 |
| 6,137,294 A * | 10/2000 | Best et al. | 324/640 |

* cited by examiner

Primary Examiner—N. Le
Assistant Examiner—Vincent Q. Nguyen
(74) Attorney, Agent, or Firm—Robert W. Gutenkauf; Peter Forrest; Malcolm D. Reid

(57) ABSTRACT

A device (10) for use in monitoring or measuring properties of a moving bed (11) of particulate material includes a sled (12) that rides or floats on the top surface (15) of the moving bed (11). A mounting structure (14) holds the sled (12) stationary with respect to the linear movement of the particulate bed (11), but permits movement of the sled (12) in a direction perpendicular to the movement of the bed (11), such as up and down when the bed (11) is moving horizontally. The sled (12) can carry on board sensors (76) to monitor the particulate material properties. Other sensors (72, 54) can be located remote from the sled (12) such as a sensor (54) to indicate displacement of the sled (12) in a direction perpendicular to the direction of travel of the moving bed (11). In one embodiment, the device includes a flume-like collector that directs particulate material through a sampling cell comprised of parallel side walls (47, 48) with the sensor sled (12) located between the sidewalls.

16 Claims, 3 Drawing Sheets

US 6,700,394 B2

DEVICE FOR USE IN MONITORING PARTICULATE FLOW

This application claims the benefit of U.S. provisional application serial No. 60/178,268 filed Jan. 27, 2000 entitled "Particulate Flow Monitoring Device."

BACKGROUND OF THE INVENTION

Many manufacturing processes produce granular or particulate products where either one or more of the properties of moisture content, temperature, density, and flow rate are important to the process or to the finished product. By way of example only and not limitation, some of these processes include:

1. Drying or cooling of grain, pelleted or extruded feeds, or extruded human foods.
2. Controlling the application of heat sensitive ingredients to cooled feeds/foods including such things as enzymes, vitamins, and other heat sensitive materials.
3. Drying or cooling of pelleted byproducts made from peat, sawdust, corn gluten or the like.
4. Monitoring and controlling moisture content of sand in concrete mixing.
5. Monitoring moisture content of pulverized coal at electric power generating plants.
6. Monitoring and controlling moisture content of ingredients entering food or feed manufacturing processes.

It is desirable to monitor the particular material property or properties that are important to the particular process or finished product. It is convenient to monitor these properties "on line" or when the material is being conveyed from one location to another, either as part of the process or expressly for the purpose of monitoring a property. Without good on line information about a product or process, automation and quality control are difficult. However, current choices of equipment for monitoring these parameters on-line are very limited or very expensive.

SUMMARY OF THE INVENTION

The invention pertains to a device for use in on-line monitoring of one or more properties of a moving stream of particulate material. The material may be moving by means of a mechanical conveyor such as a conveyor belt or under the influence of gravity, such as in an inclined chute. The monitoring device includes a sled that rides on top of the stream of moving material. In its most essential form the monitoring device includes a sled and a mounting structure. The mounting structure mounts the sled in stationary relationship to the stream of particulate material. However, the mounting structure permits the sled to "float" on the surface of the moving particulate stream, The sled can move up and down on the top of the stream, or in a direction that is substantially perpendicular to the direction of movement of the stream of material.

The sled has a base with a substantially flat bottom or under surface to skim over the surface of the particle stream in sled-like fashion. The sled has an upwardly sloped upstream edge or bow that faces the oncoming flow of particulate material. This permits the sled to ride on the top surface of the particle stream with minimal drag.

In a defined channel, the elevation of the sled above the lower surface of the process stream is a measure of the depth of the stream. In combination with the velocity of the particle stream, this is proportional to the flow rate. A measurement device can measure this depth dimension. The device can be remote from the sled and mounting structure, such as a remotely located optical measuring device. The device can be on board the sled or the mounting structure. The device can measure the vertical displacement of the sled, or the angular displacement of a mounting rod connecting the sled to the mounting structure.

The sled can carry on board measurement devices to measure other properties of the particle stream such as temperature and moisture content. A particular sensor can sense dielectric properties of the process stream which will be indicative of the moisture content and density. The linear velocity of the particle stream can be measured permitting a computation of the mass flow rate.

The device can include a flume-like collector to produce a defined process stream channel. The collector includes parallel sidewalls straddling the sled in forming a collector cell. Flow deflectors extend from the upstream edges of the parallel sidewalls in a divergent relationship. The flow deflectors form a funnel-like structure to direct the process stream into the sampling cell. A leveling device can be used to level the surface of the process stream prior to passing under the sled.

IN THE DRAWINGS

DESCRIPTION OF PREFERRED EMBODIMENTS

Figure 1:
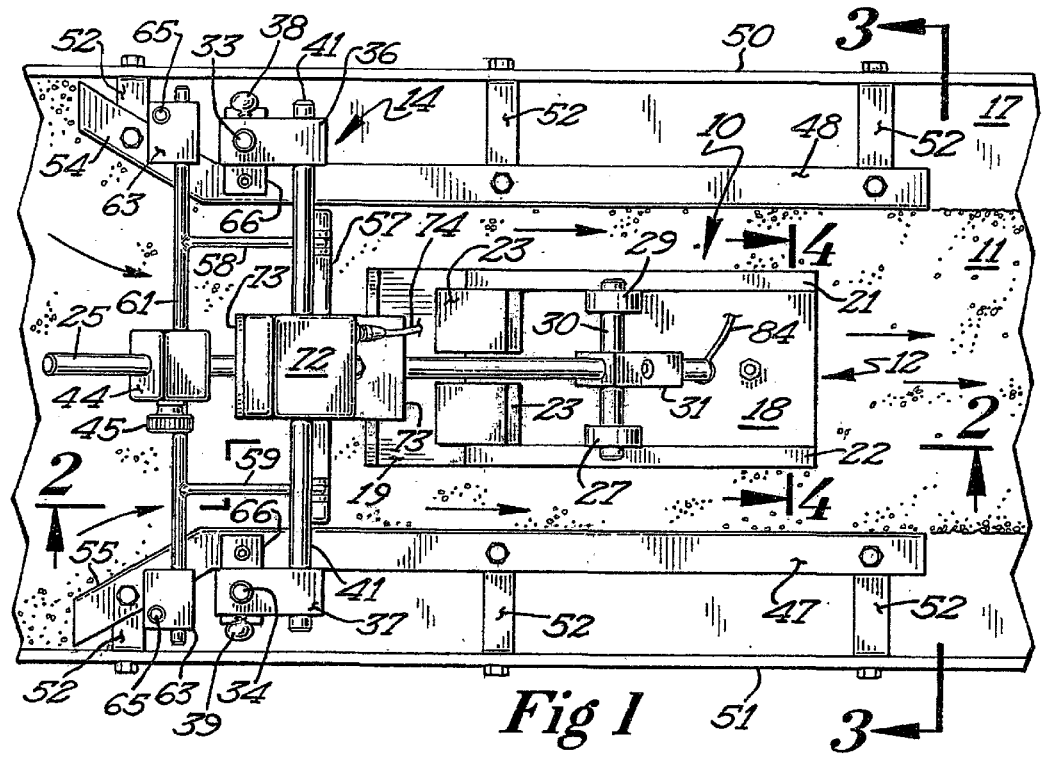
FIG. 1 is a top plan view of a device for use in monitoring particulate flow according to one form of the invention.
Figure 2:
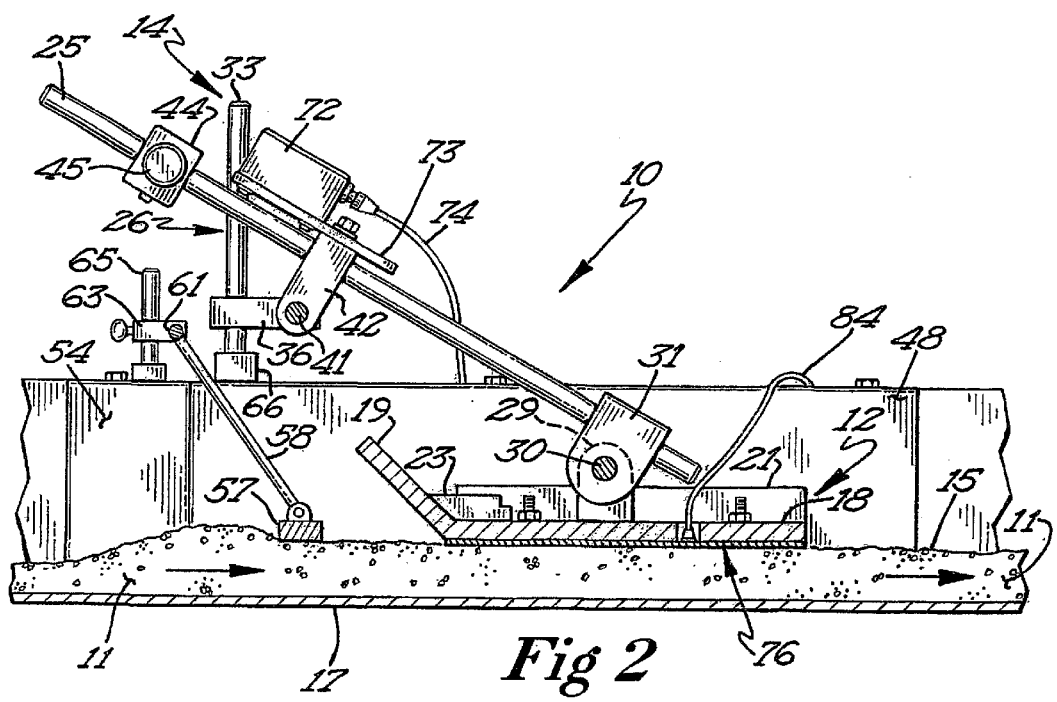
FIG. 2 is a side elevational view of the apparatus of FIG. 1 taken along the line 2—2 thereof and having portions removed for purposes of illustration.

Referring to the drawings, there is shown in FIGS. 1 and 2 a device for use in monitoring particulate flow indicated generally at 10. Device 10 is installed for use in monitoring one or more properties of a moving bed of particulate material or a process stream 11. Monitoring device 10 includes a sled 12 mounted by a mounting structure 14. Mounting structure 14 holds the sled 12 stationary with respect to movement of the process stream 11. Mounting structure 14 permits sled 12 to "float" on the top surface 15 of the process stream 11.

Process stream 11 is comprised of a moving bed of particulate material. In the example shown, the process stream 11 rides on a conveyor belt 17 although the particular means of movement of the particulate material is not an element of the invention. The process stream could be moved by other means such as other mechanical devices, or under the influence of gravity as in a chute or downspout. The "top" of the process stream refers to the uppermost surface interfacing with the sled 12. The opposite surface rides on a conveyor surface such as the conveyor belt shown or a downspout wall. The depth of the process stream is the difference between the two surfaces.

The sled 12 rides on the top surface 15 of the process stream 11. The mounting structure 14 holds the sled stationary with respect to movement of the process stream but permits free movement of the sled in a direction perpendicular to the movement of the process stream. In the case of the embodiment shown in FIG. 2, the mounting structure 14 permits free movement of the sled up and down as the depth of the process stream varies.

Sled 12 has a base 18 with a bottom that is substantially flat or flat enough to enable the base to ride on the top surface of the process stream in sled-like fashion. Sled 12 can optionally have side rails 21, 22. An upwardly directed lip or bow 19 is fixed to the upstream edge of base 18. Bow 19 is upwardly sloped in a direction facing the oncoming stream. The purpose of bow 19 is to minimize drag on sled 12. Bow 19 is shown as a separate member fixed to the base 18 by a structural members 23. Bow 19 could an integral, upwardly curved end of base 18.

Mounting structure 14 includes a pivot arm 25 pivotally connected at one end to a mounting frame 26 for rotation about a lateral axis perpendicular to the direction of movement of the process stream. The opposite or lower end of pivot arm 25 is pivotally connected to the sled 12. Sled 12 has a pair of laterally spaced apart upright mounting columns 27, 29. A pivot rod 30 extends laterally between the mounting columns 27, 29. A pivot block 31 connected to the lower end of the pivot arm 25 pivotally connects to pivot rod 30. Pivot rod 30 has a lateral axis perpendicular to the direction of travel of the process stream 12.

Mounting structure 14 includes a pair of upright mounting posts 33, 34. Carrying blocks 36, 37 secured by set screws 38,39 slidably engage the mounting posts 33, 34 for vertical adjustment. An upper pivot rod 41 extends laterally between the carrier blocks 36, 37. A fastening block 42 is connected to the upper pivot rod 41 for rotation thereon. The fastening block 42 is connected to the pivot arm 25 for rotation of arm 25 on the upper pivot rod 41.

A counterweight assembly is fixed to the upper end of mounting arm 25. The counterweight assembly includes a counterweight 44 adjustably fixed to the upper end of the pivot arm 25 by a set screw 45. Adjustment of the position of the counterweight on the arm 25 adjusts the effective weight of the sled 12. This allows control of the physical contact between the sled 12 and the flowing particulate.

The embodiment of the invention shown in FIGS. 1 through 4 includes a collector with a flume-like mouth for collection of a sample of particular material in a sensing cell. The sensing cell is defined by a pair of parallel sidewalls 47, 48, parallel to the direction of the flow of the process stream. Sidewalls 47, 48 are poised above the conveyor belt 17, held in place by suitable fastening structure. Conveyor belt assembly side rails 50, 51 straddle the conveyor belt 17. The sidewalls 47, 48 are channel shaped. Right angle fastening brackets 52 secured by nuts and bolts fasten the sidewalls 47, 48 to the conveyor belt assembly side rails 50, 51.

Flow deflectors form a funnel-type mouth to direct the process stream between sidewalls 47, 48. Flow deflectors 54, 55 extend upstream in diverging relationship from the upstream edges sidewalls 47, 48. The flow deflectors can be arranged to intercept a portion or all of the process stream for diversion through the sampling area.

A leveling apparatus includes a leveling bar that rides on top of the process stream upstream of the sled 12. The leveling bar levels the process stream for a uniform depth as it passes under the sled 12. A leveling bar 57 rides on the top of the process stream and substantially spans the width between sidewalls 47, 48. Leveling bar pivot arms 58, 59 are connected at one end to the leveling bar 57 and at the other end to a leveling bar pivot rod 61. The ends of pivot rod 61 are rotatably accommodated in mounting blocks 63 (FIG. 2) vertically adjustable on mounting posts 65.

Figure 3:
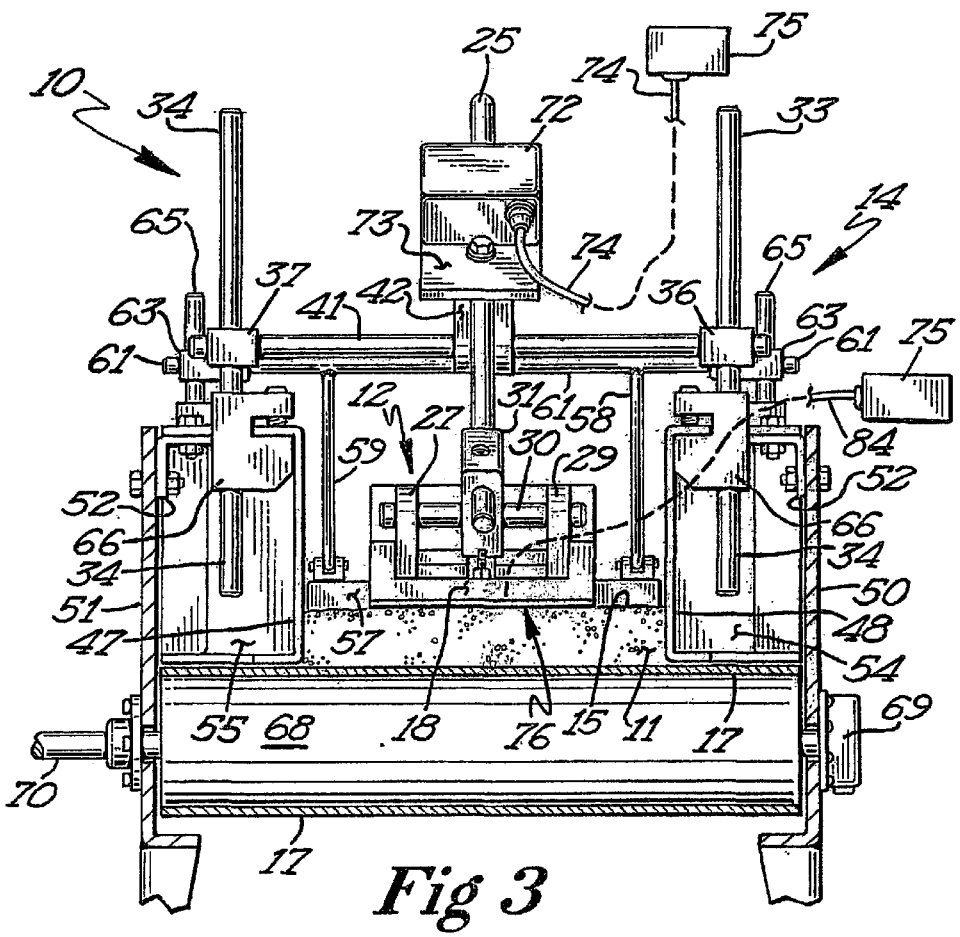
FIG. 3 is a front elevational view of the apparatus of FIG. 1 taken along the line 3—3 thereof.

FIG. 3 shows mounting clamps 66 connected to upper and outwardly turned flanges on the sidewalls 47, 48. Clamps 66 support mounting posts 33, 34. FIG. 3 also shows a conveyor belt roller 68 that carries the conveyor belt 17. A tachometer, indicated at 69, is connected to a shaft 70 of conveyor belt roller 68. Tachometer 69 measures the rotational velocity of the roller 68 which can be used to compute linear velocity of the conveyor belt 17. Other suitable devices can be employed to measure the linear velocity of the conveyor belt 17.

The device 10 is usable in monitoring certain properties of the particulate stream. These include volumetric flow rate, moisture content and temperature. In the instance where the monitored particulate stream does not have a consistent cross-section that can be mathematically described, or if it's depth does not satisfy the minimum requirements of sensors used, the particulate flow is collected and conditioned. This is done by the optional collector sidewalls and flow deflectors described above.

The depth of the process stream is measured by the vertical displacement of the sensor sled above the conveyor surface. In a defined channel the depth measurement is proportional to the volumetric flow rate of the particulate stream. Various measurement devices can be used and are considered equivalent so long as the displacement of the sled 12 is measured. The measurement devices can be on board the sled or remote from it. Tilt sensors, lasers and ultrasonic devices are only some examples of the types of devices that could be used. A device such as a tilt sensor can be used to measure the angular displacement of the pivot arm 25 connected to the sled 12. The drawings show a tilt sensor 72 mounted on a platform 73 fixed to the pivot arm 25. A suitable brand of tilt sensor is the Schaevitz AccuStar Tilt Sensor. The tilt sensor 72 sends a signal through a cable 74 to a suitable computer/controller indicated at 75. In combination with a measurement of the linear velocity of the conveyor belt 17, the volumetric flow of the particulate stream can be calculated.

Figure 4:
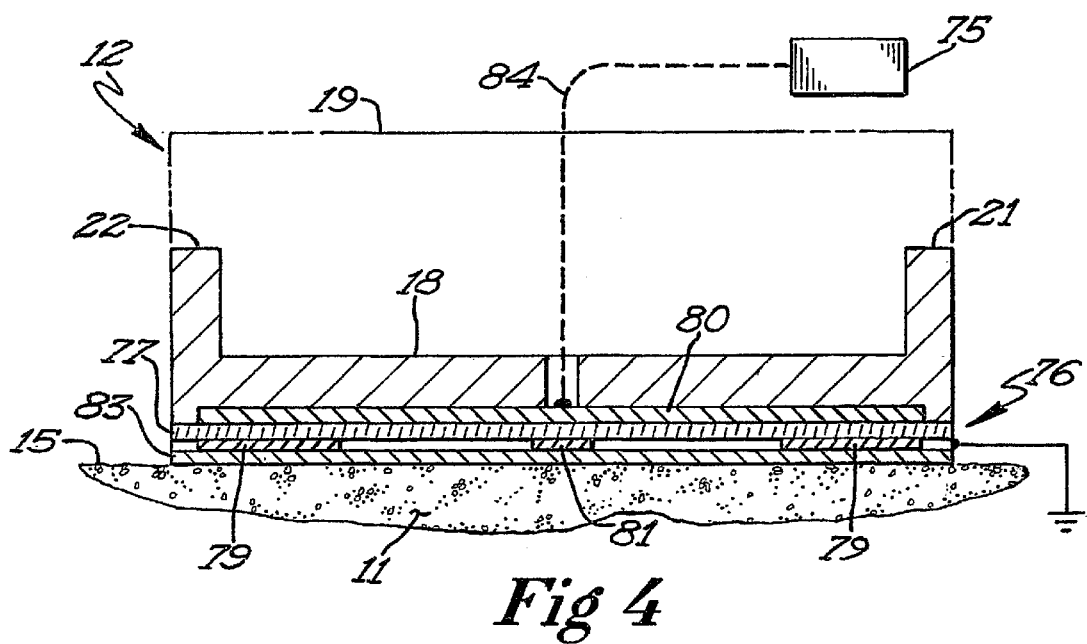
FIG. 4 is an enlarged sectional view of the base of the sled of the apparatus of FIG. 1 taken along the line 4—4 thereof.

Sled 12 can carry an array of sensors to measure various properties of the particulate stream. As shown in FIG. 4, attached to the base 18 of sled 12 and indicated generally at 76, is a shielded flat plate proximity/dielectric sensor like that shown and described in U.S. patent application Ser. No. 09/366,602, now U.S. Pat. No. 6,249,130 incorporated herein by reference.

Sensor 76 is attached to the under surface of base 18 of sled 12. Sensor 76 includes a substrate layer 77 formed of printed circuit board material or like material. A pair of sensing electrodes 79 is located on the lower surface of substrate 77 in spaced apart relationship. The sensing electrodes are coplanar and are formed of a conductive material such as a copper film. When current is applied to one electrode, electric field lines are generated to the other electrode.

A first shield electrode 80 is mounted on the side of substrate 77 opposite the sensing electrodes 79 and is positioned to intercept or block electric field lines from extending to the rear or opposite surface of the sensing element.

A second shield electrode 81 is arranged on the front surface of the dielectric substrate 77 coplanar with and between the sensing electrodes 79 and spaced parallel relation between them. The second shield electrode intercepts or blocks the field lines that are closest to the sensing electrode in order to prevent the densest portion of the electric field very near the sensing electrode from severely dominating capacitive measurements.

A protective dielectric layer 83 is provided over the sensing electrodes 79, the second shield electrode 81 and the remainder of the surface of the substrate layer 77. The protective layer 83 interfaces with the particulate stream 11.

Electric field lines originate from one of the sensing electrodes 79 and terminate at the other. These field lines are forced outwardly into the particulate stream. The changes in capacitance between the sensing electrodes is detected or measured. More specifically, the dielectric properties of the particulate stream are detected and measured. The detected signals are used for measuring certain properties of the particulate stream such as moisture content.

An electrical lead 84 (FIG. 2) extends from sensor 76 to a suitable computer/controller 75 for processing.

In the use of the invention, sled 12 is mounted by suitable mounting structure so as to ride or "float" on the top of a particulate stream. The mounting structure can be comprised of rigid or flexible members that attach from either above or beneath the sensor sled. The criteria is that the sensor sled be held stationary with respect to the moving particulate stream and be permitted to rise and fall according to the variation of the depth of the particulate stream.

The particle stream flows under the sled 12. The following data can be generated: vertical displacement of the sled, indicative of volumetric flow rate; particulate temperature; particulate dielectric properties indicating the moisture content, density or other such characteristics. The effective weight of the sled can be adjusted to increase contact between the sled surface and the monitored flowing particulate material to improve sensitivity. This can be done through adjustment of the counterweight 44 on the pivot arm 25 in the embodiment of the mounting structure shown. Other equivalent means to adjust the effective weight of the sled could be employed.

If the invention is used on a conveyor belt or similar device, a means for monitoring the linear velocity of the particulate stream can be used. In the example illustrated, a tachometer mounted on a drive roller is used.

When desirable, a flume type collector device can be used in order to create a mathematically definable channel of particulate matter. The leveling bar assembly is used to provide a uniformly flat cross-section to the particulate flow in a sensing cell defined by the sidewalls 21, 22.

Figure 5:
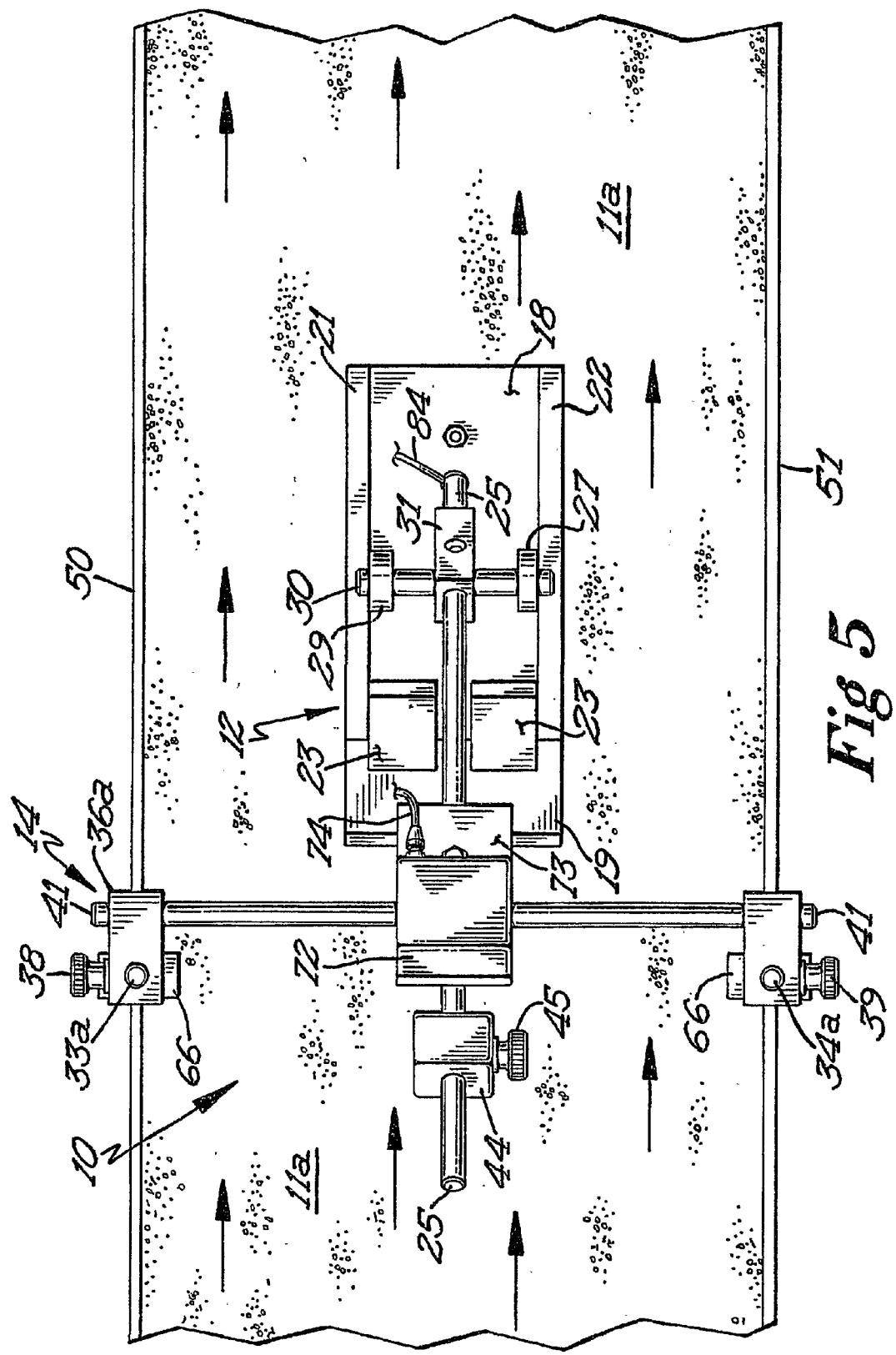
FIG. 5 is a top plan view of a modification of the invention of FIG. 1.

FIG. 5 shows an embodiment of the invention without the flume-type collector. The sled 12 rides on the top of the particulate process stream 11A that is confined between conveyor assembly sidewalls 50,51. Pivot arm 25 rotatable connects the sled 12 to the upper lateral pivot rod 41. Pivot rod 41 is mounted in carrying blocks 36A and 37A that are secured to mounting posts 33A, 34A. A sample of the particulate stream passes under the sled 12.

The embodiments of the invention in which an exclusive property or privilege is claimed are defined as follows:

1. A device for use in monitoring one or more particulate material properties of a moving bed of particulate material on a conveyor surface, comprising:

a sensor sled having a base with a substantially flat bottom for riding on the top of moving bed of particulate material, and an upwardly sloped front wall for facing upstream relative to the moving bed;

a mounting structure connected to the sled positioning the sled relative to the conveyor surface to ride on top of the bed with the front wall facing upstream, said mounting structure including a mounting member attached to the sled to hold the sled stationary with respect to linear movement of the bed and permit displacement of the sled in a direction perpendicular to the movement of the bed as the depth of the bed varies on the conveyor surface;

at least one sensor positioned on the sled to measure a property of the particulate material.

2. The device of claim 1 wherein:

the mounting member comprises a pivot arm.

3. The device of claim 2 wherein:

the mounting structure includes an upper pivot rod extending laterally across and above the conveyor surface, said pivot arm connected at an upper end to the upper pivot rod.

4. The device of claim 3 including:

a lower pivot rod attached to the sled parallel to the upper pivot rod, said pivot arm connected at one end to the lower pivot rod.

5. The device of claim 3 wherein:

said mounting structure includes a mounting frame having at least one upright mounting post, a mounting block adjustable attached to the mounting post, said upper pivot rod connected to the mounting block.

6. The device of claim 3 wherein:

said mounting structure includes a mounting frame having a pair of upright mounting posts straddling the conveyor surface, said upper pivot rod connected between the mounting posts.

7. The device of claim 3 including:

an apparatus for measuring the angular displacement of the pivot arm in order to calculate the depth of the bed.

8. The device of claim 7 wherein:

said apparatus to measure the angular displacement of the pivot arm comprises a tilt sensor mounted on the pivot arm.

9. The device of claim 1 including:

a collector having parallel sidewalls mounted in straddling relationship to the sled and poised above the conveyor surface parallel to the direction of travel of the bed; and flow deflectors extending in divergent relationship from upstream edges of the sidewalls.

10. The device of claim 9 including:

a leveling bar assembly including a leveling bar mounted laterally of the conveyor surface and upstream of the sled to level particulate material prior to its passing under the sled.

11. The device of claim 1 wherein:

said sensor includes a dielectric properties sensor.

12. A device for use in monitoring one or more properties of particulate material of a moving bed, comprising:

a conveyor surface to carry the moving bed of particulate material;

a sensor sled having a base with a substantially flat bottom for riding on the top surface of the bed, and an upwardly sloped front wall for facing upstream relative to the moving bed;

a mounting structure including an upper pivot rod mounted laterally across and above the conveyor surface;

said mounting structure including a pivot arm connected at one end to the upper pivot rod and at the opposite end to the sled to hold the sled stationary relative to linear movement of the particulate bed and permit displacement of the sled in a direction perpendicular to the movement of the bed as the depth of the bed varies; and at least one sensor positioned on the sled to measure a property of the particulate material.

13. The device of claim 12 wherein:

said sensor included a dielectric properties sensor fixed to the under surface of the base.

14. The device of claim 13 wherein:

said sled has a second pivot rod parallel to the first pivot rod, said pivot arm connected to the second pivot rod.

15. The device of claim 14 including:

a device for measurement of the displacement of the sled from the conveyor surface.

16. The device of claim 15 wherein:

the device for measurement of the displacement of the sled from the conveyor surface comprises a tilt sensor mounted on the pivot arm.

* * * * *